United States Patent
Gierke et al.

(10) Patent No.: US 10,188,133 B2
(45) Date of Patent: Jan. 29, 2019

(54) GEL CAPSULE CONTAINING STEROL AND SOLUBILISING AGENT

(71) Applicant: BASF SE, Ludwigshafen (DE)

(72) Inventors: Juergen Gierke, Wain (DE); Martin Weidner, Kuenzell (DE); Marianne Heer, Lampertheim (DE); Thorsten Schmeller, Wachenheim (DE); Thrandur Helgason, Mannheim (DE); Heribert Bohn, Wattenheim (DE); Anja Weiland, Maxdorf (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/568,493

(22) PCT Filed: Apr. 20, 2016

(86) PCT No.: PCT/EP2016/058683
§ 371 (c)(1),
(2) Date: Oct. 23, 2017

(87) PCT Pub. No.: WO2016/169941
PCT Pub. Date: Oct. 27, 2016

(65) Prior Publication Data
US 2018/0110254 A1    Apr. 26, 2018

(30) Foreign Application Priority Data

Apr. 23, 2015 (EP) ..................... 15164868
Apr. 28, 2015 (EP) ..................... 15165398

(51) Int. Cl.
| | | |
|---|---|---|
| A23D 7/00 | (2006.01) |
| A23L 33/11 | (2016.01) |
| A61K 45/06 | (2006.01) |
| A61K 9/48 | (2006.01) |
| A61K 31/56 | (2006.01) |
| A23P 10/30 | (2016.01) |
| A23L 33/12 | (2016.01) |

(52) U.S. Cl.
CPC ............ *A23L 33/11* (2016.08); *A23L 33/12* (2016.08); *A23P 10/30* (2016.08); *A61K 9/4858* (2013.01); *A61K 31/56* (2013.01); *A61K 45/06* (2013.01); *A23V 2002/00* (2013.01); *A23V 2200/238* (2013.01); *A23V 2250/1842* (2013.01); *A23V 2250/1882* (2013.01); *A23V 2250/21368* (2013.01); *A61K 2300/00* (2013.01)

(58) Field of Classification Search
CPC ...................................... A23D 9/013
USPC ....................................... 426/611
See application file for complete search history.

(56) References Cited

U.S. PATENT DOCUMENTS

| | | | |
|---|---|---|---|
| 5,505,961 A | 4/1996 | Shelley et al. |
| 5,569,466 A | 10/1996 | Tanner et al. |
| 6,770,293 B2 | 8/2004 | Angel et al. |
| 6,783,770 B2 | 8/2004 | Angel et al. |
| 6,790,495 B1 | 9/2004 | Tomka et al. |
| 2003/0085487 A1 | 5/2003 | Tanner et al. |
| 2003/0232076 A1 | 12/2003 | Makino et al. |
| 2004/0060258 A1 | 4/2004 | Stolz |
| 2005/0153948 A1 | 7/2005 | Spilburg |
| 2006/0035871 A1 | 2/2006 | Auweter et al. |
| 2007/0254088 A1* | 11/2007 | Stewart ............... A21D 2/14 426/611 |
| 2010/0098784 A1 | 4/2010 | Engel |
| 2010/0283178 A1 | 11/2010 | Kolter |
| 2010/0291197 A1 | 11/2010 | Schwab |
| 2016/0324745 A1 | 11/2016 | Helgason et al. |

FOREIGN PATENT DOCUMENTS

| | | |
|---|---|---|
| DE | 2237545 A1 | 2/1974 |
| DE | 10253111 A1 | 5/2004 |
| EP | 1136070 A1 | 9/2001 |
| EP | 1138322 A2 | 10/2001 |
| EP | 2042165 A1 | 4/2009 |
| EP | 2042180 A1 | 4/2009 |
| EP | 1926480 B1 | 7/2013 |
| WO | WO-9956558 A1 | 11/1999 |
| WO | WO-2002074861 A1 | 9/2002 |
| WO | WO-2007116062 A1 | 10/2007 |
| WO | WO-2014202754 A1 | 12/2014 |
| WO | WO-2016169942 | 10/2016 |

OTHER PUBLICATIONS

Yoo et al. CAS: 148:120693, 2007.*
International Preliminary Report on Patentability for PCT/EP2016/058683 dated Oct. 24, 2017.
International Search Report for PCT/EP2016/058683 dated Jul. 8, 2016.
Stegmann, A.S., "Hartgelatinekapseln—Aktueller Stand und Perspektiven", PZ PRISMA, 1998, vol. 5, No. 1, pp. 42-56.
Acuff, et al., "The Lipid Lowering Effect of Plant Sterol Ester Capsules in Hypercholesterolemic Subjects", Lipids in Health and Disease, vol. 6, Issue 11, Apr. 9, 2007, 11 pages.
Anonymous, "VegaPure 95E", internet citation, XP002759247.
Bauer, et al., "Lehrbuch der Pharmazeutischen Technologie", 8th edition, Chapter 14, Subchapter 6, pp. 344-355.
Bauer, et al., "Lehrbuch der Pharmazeutischen Technologie: Chapter 4—Die Herstellung von Hart- und Weichgelatinekapsel", pp. 58-82.
Eith, et al., "The Injection-Moulded Capsule", Drug Development and Industrial Pharmacy, vol. 12, Issues 11-13, 1986, pp. 2113-2126.
Fahrig, et al., "Die Kapsel", Wissenschaftliche Verlagsgesellschaft MBH Stuttgart, 1983, pp. 58-82.

* cited by examiner

Primary Examiner — Rei Tsang Shiao
(74) Attorney, Agent, or Firm — Drinker Biddle & Reath LLP

(57) ABSTRACT

The present invention relates to gel capsules comprising sterol and solubilizer for use as food supplement or as pharmaceutical.

19 Claims, 5 Drawing Sheets

Figure 1:
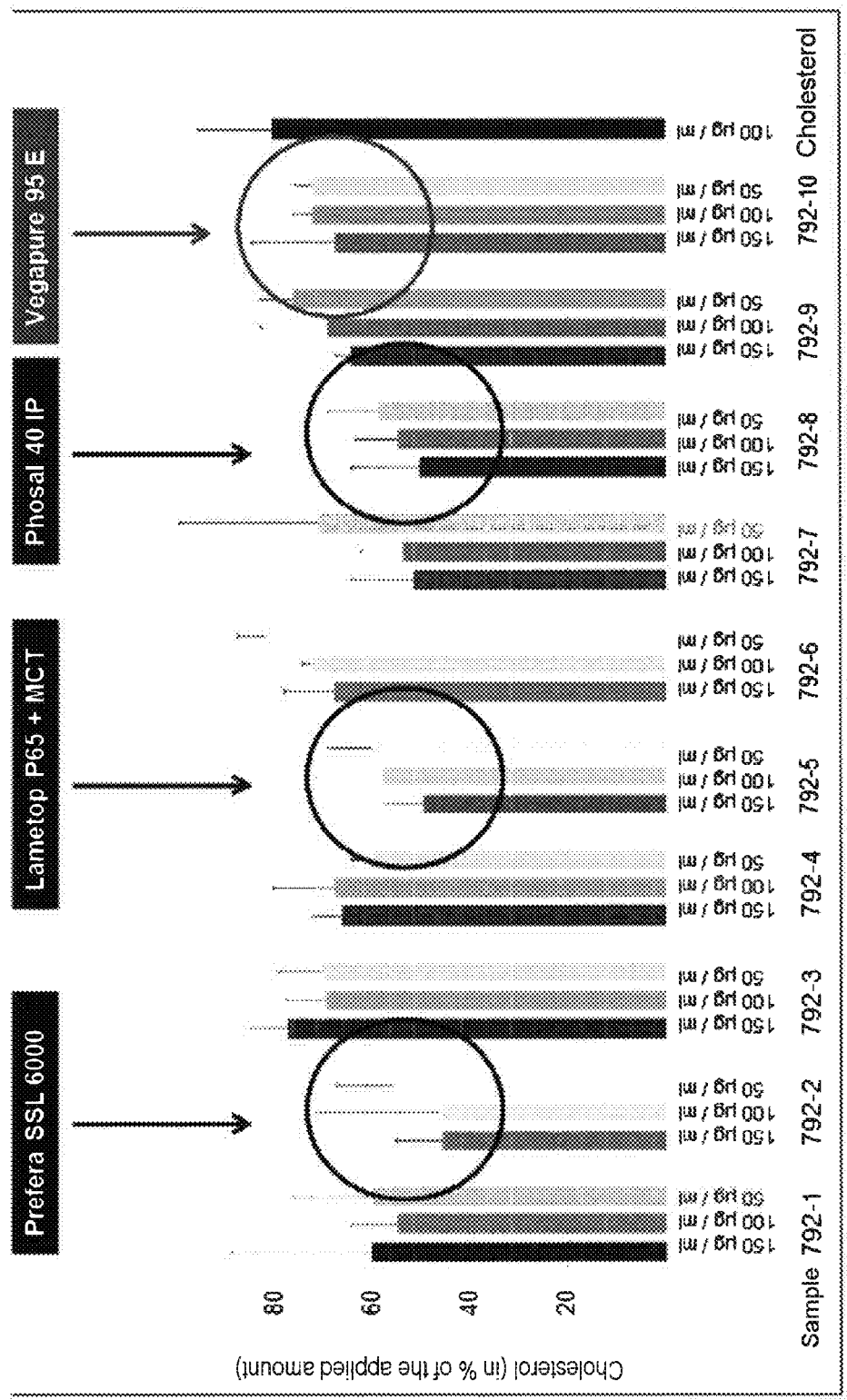

Cholesterol content of the basal recipient medium after 6 hours (in % of the applied starting concentration)

Cholesterol content of the basal recipient medium after 24 hours (in % of the applied starting concentration)

Infrared spectra of the micelle solutions of cholesterol ("CHOL") alone and in combination with the tested formulations PCA analysis of the micelle solutions of cholesterol (CHOL) alone and in combination with various test substances (C1 to C10)

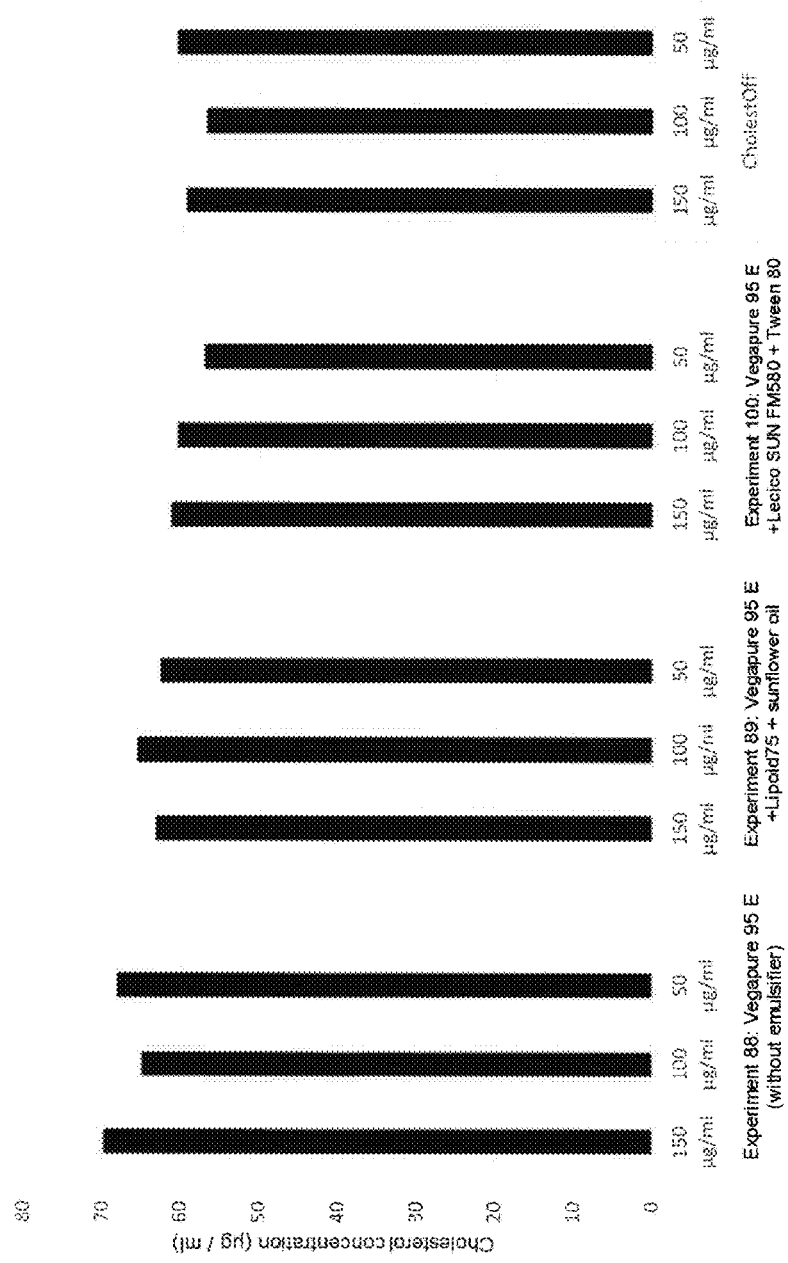

GEL CAPSULE CONTAINING STEROL AND SOLUBILISING AGENT

CROSS-REFERENCE TO RELATED APPLICATIONS

This application is a national stage application (under 35 U.S.C. § 371) of PCT/EP2016/058683, filed Apr. 20, 2016, which claims benefit of European Application Nos. 15164868.0, filed Apr. 23, 2015, and 15165398.7, filed Apr. 28, 2015, all of which are incorporated herein by reference in their entirety.

The present invention relates to gel capsules comprising sterol and solubilizer for use as food supplement or as pharmaceutical.

Gel capsules as such are known: there are so-called hard capsules and soft capsules. The production thereof, the input materials used therefor and the production thereof are well known to a person skilled in the art.

The use of gel capsules comprising sterols as food supplement or as pharmaceutical is already likewise known.

Since sterols are only very sparingly soluble in water, an oil is generally used as solvent.

Sterol esters are better soluble, but are generally likewise presently dissolved in oil or a fat substance.

Since the sterols and sterol esters are thus used such that they are formulated in oil, a significant proportion of the formulation is an oil. However, the amount of formulation which can thus be supplied per dosage unit, i.e., for instance a gel capsule, is limited owing to the maximally acceptable size of the gel capsule. If only a portion of this formulation is used up by oil, the amount of suppliable sterol or amount of sterol ester is further limited. In order to provide the recommended daily amounts of free sterol in the amount of 2 to 3 g per day per adult, what is striven for is the need to supply a lowest possible number of gel capsules per day, and the gel capsules should also additionally be as small as possible; this firstly increases "compliance", i.e., the observance of the correct dosage by the patient, and thus improves as a whole the efficacy of the treatment. Furthermore, in the case of food supplements, acceptance by the user is improved and thus ultimately likewise the efficacy of the intervention.

In order to improve the effectiveness of the sterol ester formulation, the sterol esters and the other ingredients must form a fine emulsion, specifically even at low shear rates and the pH in the stomach. This is achieved in the pharmaceutical industry in the case of pharmaceutical formulations by self-emulsifying systems. However, this involves using very large amounts of diluting substances and emulsifiers. Similarly, in the case of pharmaceutical formulations, there is regulatory approval for a multiplicity of emulsifiers, and so the adjustment of the formulation to achieve a self-emulsifying system is, in relative terms, simpler than in the case of foodstuffs. Furthermore, the amounts of pharmaceutically active substance to be administered in such self-emulsifying systems per dose are usually distinctly lower than is the case for substances in the food sector.

In the case of the administration of sterol esters per dose, the amounts are in the range of about 1 to 3 grams per dose, and the total amount of formulation to be dosed is therefore already very large when the dose is to be formulated as a capsule. In the food sector, since, in comparison with pharmaceutical applications, the number of emulsifiers and of surfactants is greatly limited from a regulatory point of view and the breadth of properties of the available emulsifiers is thus also very limited, it is a distinctly greater challenge to achieve a self-emulsifying system with small amounts of foodstuff-approved emulsifiers and surfactants. The low pH in the stomach reduces the activity of the anionic surfactants by neutralization. Therefore, there is currently lack of availability of an effective formulation of sterol esters in capsules which allows a single or maximally double administration (i.e., the administration of one or at most two capsules per day) in order to thus supply the daily amount of sterol in the form of sterol esters.

Therefore, it is desirable to improve the formulation of sterols and sterol esters in gel capsules to the extent that the proportion by weight of sterol based on the free sterol is maximized in such a formulation for one gel capsule.

It is known that sterols are, inter alia, phytosterols, i.e., sterols obtained from plants.

In principle, sterol esters are all esters with all conceivable carboxylic acids. However, only the esters with fatty acids are customarily of interest in the area of food and health.

It is known how to produce sterol esters of fatty acids; the most commonly used method is the production from sterols and fatty acids by esterification. By means of the reaction, it is possible to control in virtually any desired manner the conversion and thus also the degree of purity of the sterol esters. What are customarily striven for are at least 80 percent conversion to the sterol ester conversions of up to virtually 100 percent are known and technically feasible. A higher purity can also be achieved by cleanup such as crystallization, winterization, etc. All such methods are well known.

What have been found are formulations for gel capsules comprising substantially sterol ester and emulsifier (also referred to as solubilizer) and also gel capsules comprising said formulations.

In this connection, "substantially" means that the total proportion of the formulation is at least 61 percent by weight.

In the context of this invention, "solubilizer" generally refers to substances which act in an emulsifying and/or stabilizing manner, and are also synonymously referred to in the context of this invention as "emulsifier" or "surfactant".

In principle, it is possible to use as sterol ester any sterol ester from any sterol. Preference is given to using sterols from plants ("phytosterols"), which are well known to a person skilled in the art. In the context of this invention, the term "sterols" and "phytosterols" also encompasses the hydrogenated analogs thereof, the "stanols", unless explicitly described otherwise.

Particular preference is given to the (non-subsequently hydrogenated) sterols.

The sterols and stanols, especially sterols, are preferably esterified with fatty acids. In principle, any fatty acid is possible as fatty acid. Preference is given to fatty acids obtained of natural origin, especially those from plants and of marine origin, or the fatty acids respectively corresponding thereto, but produced synthetically. Particular preference is given to fatty acids of plant or marine origin. The fatty acids can be used as pure substance or as substance comprising predominantly one or more few fatty acids, or else as mixture of many different fatty acids.

Preference is given to using fatty acids which have an additional health benefit. Such fatty acids having an additional health benefit are, in particular, monounsaturated and polyunsaturated fatty acids such as omega-3 fatty acids, EPA, and DHA; all these fatty acids, their production, obtainment and cleanup are well known to a person skilled in the art.

Sterol esters in the context of the present invention can also comprise free sterols, i.e., nonesterified sterols. The sterol esters used are mixtures of sterol esters and free sterols, the sterol ester content being preferably at least 80, particularly preferably at least 90, very particularly preferably at least 95 and especially at least 98 mol percent (based on the sterol portion in the ester) and it being possible for said sterol ester content to be all values between these ranges and up to 100 percent.

The formulations according to the invention for gel capsules and the gel capsules comprising said formulations therefore preferably comprise sterol esters, especially sterol esters with monounsaturated or polyunsaturated, particularly preferably polyunsaturated, fatty acids of preferably plant or marine origin, at least one solubilizer, preferably selected from polysorbates such as polysorbate 20, 40, 60 and 80, lecithins and sodium stearoyl-2-lactylates, particularly preferably selected from polysorbate 80 (polyoxyethylene (20) sorbitan monooleate, E433), lecithin and sodium stearoyl-2-lactylate having a degree of esterification of 100 to 140, very particularly preferably polysorbate 80 and/or lecithin. Particular preference is given to using at least two different emulsifiers.

Lecithin in the context of this invention means a composition comprising a proportion of lecithin preferably obtained from natural sources of any vegetable or animal source. Such sources and obtaining lecithins therefrom are well known to a person skilled in the art, for instance from eggs, soy, sunflowers, rapeseed. Lecithin in the context of this invention is preferably a mixture comprising lecithin fractions, lysolecithin (such as hydrolyzed lecithin, enzymatically treated lecithin) and/or phospholipids, obtained from all vegetable and/or animal sources, preferably vegetable sources such as rapeseed, sunflowers and/or soy, particularly preferably such a mixture obtained from soybeans, very particularly preferably such a mixture comprising at least 40, 45, 50, 55, 60, 65, 70 or 75 or greater percent of phosphatidylcholine and at least 3, 4, 5, 6 or 7% phosphatidylethanolamine—where the total amount always comes to 100 percent—for example the commercial products of the Lecico range such as the soy lecithins Lecico F 600, Lecico F 580, Lecico F300, Lecico F 200, Lecico F 100, Lecico P900, Lecico P 700, Lecico P 300, the sunflower lecithins Lecico SUN 400, Lecico SUN FM 580, the rapeseed lecithin Lecico RAP 200, of the Lipoid and Phospholidon ranges, for instance of the, Lipoid P45, Lipoid P75, Lipoid P75-3, Lipoid P100, Upoid H100, Lipoid R100, Lipoid P100-3, Lipoid 545, Lipoid S75, Phospholidon 80H, Phospholidon 90H, Phospholidon 90G, preferably each with at least 60, 65, 70 or 75, 80, 85, 90, 95 or greater percent of phosphatidylcholine such as in particular Lipoid P75, Lipoid S75, Lipoid P75-3, Lipoid P100-3, Phospholidon 80H, Phospholidon 90H, Phospholidon 90G, very particularly preferably those with about 65 to 75, especially about 70 percent proportion of phosphatidylcholine.

Furthermore, the formulations for gel capsules and the gel capsules comprising said formulations can also comprise water, alcohols or the mixtures thereof. Preferably, formulations comprising lecithin as solubilizer also comprise water and/or alcohols, particularly preferably predominantly or very predominantly alcohols. In this connection, "very predominantly" means that the alcohols may comprise additionally residual amounts of water. Said residual amounts are preferably less than 5, less than 4, less than 3, less than 2, less than 1 or even less than 0.5 percent proportion by weight in the alcohol.

In another embodiment, the formulations for the gel capsules comprising lecithin as solubilizer comprise oils, especially plant oils such as sunflower oil. However, the oil amounts are preferably small in comparison with the amount of sterol ester and only sufficiently large to achieve a uniform dissolution of the sterol ester and of the lecithin.

Further ingredients are possible for the formulations according to the invention, though they lower the amount of formulatable sterol. Therefore, preference is given to only those additives necessary for the purposes of formulation, for instance stabilizers for the sterol esters, such as antioxidants, and also sugar esters, for instance mono-, di-, and triesters of fatty acids and sugars, preferably sucrose, preferably monoesters of palmitic acid and sucrose, monoesters of stearic acid and sucrose and/or monoesters of oleic acid and sucrose. Customary and suitable antioxidants are well known to a person skilled in the art. The above formulations according to the invention for gel capsules and the gel capsules comprising said formulations therefore preferably comprise small amounts of antioxidants, preferably selected from sterically hindered phenolic antioxidants such as t-butylhydroxytoluene, t-butylhydroxyanisole, t-butylhydroxyquinone; tocopherols such as alpha-, beta-, gamma- and delta-tocopherol or mixtures comprising at least two of these tocopherols; alpha-, beta-, gamma- and delta-tocotrienols mixtures comprising at least two of these tocotrienols; natural extracts comprising at least one of the aforementioned substances and/or phenolic diterpenes such as carnosol, carnosic acid, polyphenols such as epigallocatechin gallate, tannic acid and/or isoflavones; especially of tocopherols, ascorbic acid or isoascorbic acid or the appropriate derivatives thereof such as esters with fatty acids, such as ascorbyl palmitate and ascorbyl stearate. Preference is given to tocopherols and ascorbyl fatty acid esters, especially tocopherols and ascorbyl palmitate.

The formulations according to the invention comprise the following amounts of substances:

Sterol Ester:

At least 60, 65 or preferably at least 70, particularly preferably at least 75, very particularly preferably at least 80, such as especially preferably at least 85 or even at least 88 percent by weight, based on the total formulation, which serves as filler material for gel capsules, such as, for example, 60, 61, 62, 63, 64, 66, 67, 68, 69, 71, 72, 73, 74, 76, 77, 78, 79, 81, 82, 83, 84, 86, 87, 89, 90.

Solubilizer

In the case of lecithins and mixtures comprising lecithin fractions and phospholipids: at least 1, preferably at least 1.1, particularly preferably at least 1.2, very particularly preferably at least 1.3 and especially at least 1.4 percent by weight, as lower limit, and up to 20 percent by weight, preferably up to 15, particularly preferably up to 10 and especially preferably up to 5 percent by weight, as upper limit, based in each case on the total formulation, which serves as filler material for gel capsules, such as, for example, 1.5. 1.6, 1.7, 1.8, 1.9, 2.0, 2.1, 2.2, 2.3, 2.4, 2.5, 2.6 2.7, 2.8, 2.9, 3.0, 3.5, 4.0, 4.5, 5.0 and all values in-between;

In the case of polysorbates such as polysorbate 80 and stearoyl-2-lactylates: at least 5, preferably at least 5.5, particularly preferably at least 6.0, very particularly preferably at least 6.5 and especially at least 7.0 percent by weight, based on the total formulation, which serves as filler material for gel capsules, such as, for example, 5.1, 5.2, 5.3, 5.4, 5.6, 5.7, 5.8, 5.9, 6.1, 6.2, 6.3, 6.4, 6.6, 6.7, 6.8, 6.9, 7.1, 7.2, 7.3, 7.4, 7.5, 7.6, 7.7, 7.8, 7.9, 8.0, 8.1, 8.2, 8.3, 8.4, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0 and all values in-between.

Water

Water can be present in amounts of 0 to 25 percent by weight. When using polysorbates as sole solubilizers, use is made of water amounts of 0 to 15 percent by weight, preferably zero to 10 percent by weight, based on the total formulation, which serves as filler material for gel capsules, and also all values between these end points. In this connection, "small amount" means that not more than 10, preferably not more than 5 percent water are present in the formulation.

When using lecithins and mixtures comprising lecithin fractions and phospholipids as sole solubilizers, use is made of water amounts of 0 to 25 percent by weight, preferably 5 to 23 percent by weight and particularly preferably 10 to 20 percent by weight, based on the total formulation, which serves as filler material for gel capsules, and also all values between these end points. In this connection, "small amount" means that not more than 20, preferably not more than 15 percent water are present in the formulation.

Oils:

An oil or multiple oils can be present in amounts of 0 to 25 percent by weight, though preferably not more than 20, particularly preferably not more than 15, very particularly preferably not more than 10 and especially preferably not more than 5 percent by weight, based on the total formulation. "Small amount" means that not more than 10, preferably not more than 5 percent oil are present in the formulation.

In principle, suitable oils are all oils (i.e., triglycerides) of natural and synthetic origin, but preferably of natural origin, especially of plant or marine origin, very especially of plant origin, such as oils from sunflowers, linseed, flax, thistle, almond, rapeseed, coconut, palm, etc. or the mixtures, as are well known to a person skilled in the art. Preference is given to using oils having low proportions of saturated fatty acids and/or high proportions of unsaturated and especially polyunsaturated fatty acids, since they bring about an additional health advantage when used, whereas saturated fatty acids and especially trans-fatty acids should preferably be avoided to the extent that is technically possible and/or commercially (i.e., especially in terms of costs) bearable.

Therefore, preference is given to fatty acid mixtures having low amounts of trans-fatty acids, preferably less than 5, 4, 3, 2, or even 1 percent or less trans-fatty acids, and/or, preferably and having amounts of saturated fatty acids of less than 7 percent, preferably less than 6, 5, 4, 3 or even 2 or 1 percent of saturated fatty acids, based in each case on the total mass of fatty acids in the mixture.

Particularly preferably, the formulations do not comprise any oils.

As further ingredients, preference is given to using: ascorbyl palmitate and sugar esters, each in amounts of up to 20, preferably up to 15, particularly preferably up to 10 and especially up to 5 percent by weight, based on the total formulation, which serves as filler material for gel capsules. Preference is given to using, in each case, at least 1 percent, such as, for example, 1.5, 2, 2.5, 3, 3.5, 4 or 4.5 percent by weight.

The present invention therefore also encompasses a process for producing a formulation according to the invention, preferably for producing one of the preferred embodiments of the formulation such as in particular embodiments A and AA.

Such a process comprises, preferably consists of, the following steps: a) adding sterol ester and solubilizers individually in succession, in pairs, with two or more at the same time or with all at the same time, preferably all in succession, particularly preferably adding the sterol ester as first substance and subsequently adding the other substances before, during or after the heating in step b), particularly preferably before the heating in step b), in a mixing vessel; b) heating the individually initially charged substance or a mixture of two or more substances to a temperature above the melting point of the sterol ester; c) mixing the heated mixture at 500 to 2500 rpm for a period of 1 to 60 minutes in order to obtain a uniform mixture.

In principle, possible gel capsules include all types of hard and soft capsules, produced from substances of natural origin, for instance plant and/or animal origin, and of synthetic origin, for instance polymers produced synthetically or produced by means of biotechnological methods. Preference is given to gel capsules composed of plant substances and those composed of synthetic polymers.

Such materials, their production and obtainment and also their processing to gel capsules is well known to a person skilled in the art. Fundamental overviews can be found, for instance, in the *Lehrbuch der Pharmazeutischen Technologie* [Textbook of pharmaceutical technology], for instance in chapter IV, "*Die Herstellung von Hart-und Weichgelatinekapselrt*" [The production of hard and soft gelatin capsules], author Kurt H. Bauer, Freiburg, pages 58 to 82, or in the 8th edition of this textbook in chapter 14, subchapter 6, pages 344 to 355, and also many other standard textbooks. Hard capsules, for example, are distinguished by the fact that the capsules are produced as two-part, stuck-together empty capsules which are filled and closed only after production. In the majority of cases, the hard capsules are produced from aqueous solution in the so-called dipping method (S. Stegmann, P Z Prisma, 5, 42-56, 1998). A prior-art overview of injection molding for producing pharmaceutical hard capsules from starch or gelatin is given by L. Eith et al. in Drug Dev. Ind. Pharm., 12, 2113-2126 (1986). The completely different methods for producing hard and soft gelatin capsules are described in W. Fahrig and U. Hofer, *Die Kapsel* [The capsule], Wissenschaftliche Verlagsgesellschaft mbH Stuttgart, 1983, pages 58-82.

Capsules and their production and use can likewise be found in many patent specifications. Known manufacturers of capsules for especially pharmaceutical applications, food supplements, etc., are the companies Catalent (R. P. Scherer has merged into Catalent), Banner, Capsugel, Accucaps, Swiss Caps (merged into Aenova). Corresponding publications and patent applications and patents are known from these and many other companies.

The following may be mentioned by way of example: WO2014/202754 discloses soft capsules comprising acyl gellan gum, starch and plasticizer; US 20010098784 discloses capsules comprising plant preparations; U.S. Pat. No. 6,790,495B discloses the production of starch-containing soft capsules and an apparatus for the production thereof; WO2007/116062 discloses capsules or melt extrudates comprising a plant extract; US2010291197 discloses capsules produced by melt extrusion and composed of polymer material; EP2042180A1 discloses soft capsules comprising phytosterols, 10 to 100 percent triglyceride, 1 to 40 percent of an emulsifier with HLB value greater than 12 and 1 to 80 percent of a coemulsifier with HLB value less than 11, self-emulsifying filler and free of water; WO2002074861 discloses the use of a polyol as gel former and also cold-water-soluble gelatin gel capsules therefrom; US2004060258 discloses the production of capsules, especially soft capsules, by means of the rotary-die method; DE2237545A1 discloses a process for producing microcapsules by evaporating a polymer solution in an organic solvent; EP1138322A2 discloses hard capsules and EP1136070 (A1) discloses soft capsules, each, for example for pharmaceutical applications, comprising polymers of vinyl esters and optionally further monomers, structure-improving excipients and also further customary shell constituents, their use and production; EP1926480 (B1) discloses soft capsules and their production with soft capsule shells based on polyvinyl ester-polyethylene glycol graft copolymers; US55699466 A discloses filling compositions for elastic soft capsules; U.S. Pat. No. 5,505,961A discloses gelatin capsules; US2003085487A discloses an apparatus for producing soft capsules; US2003232076A discloses chewable soft capsules.

The present invention therefore also encompasses a process for producing a gel capsule comprising the formulation according to the invention, preferably one of the preferred embodiments of the formulation such as in particular embodiments A and AA. In principle, all materials and production methods and steps that are known to a person skilled in the art are possible as gel capsule material, provided there is compatibility with the formulation according to the invention.

This compatibility can be easily assessed, firstly on the basis of the substances used for the formulation and the capsule materials, and secondly by means of simple experiments with appropriate capsule materials.

As shown in the examples, the use of individual emulsifiers did not yield good self-emulsifying results. However, when two emulsifiers were mixed, very good results and self-emulsifying systems were obtained. This was especially surprising in the case of SUN FM 580 (lecithin) and Systerna SP 70 (sugar ester), since the Systerna product alone is insoluble in the formulation and had to be dispersed using rotor-stator mixers. The use of a small amount of Systerna product improved the self-emulsification drastically, however.

It was similarly found that the addition of an ascorbic fatty acid ester such as ascorbyl palmitate and/or ascorbyl stearate, especially ascorbyl palmitate, to a lecithin-comprising formulation distinctly improved the self-emulsifying properties in the stomach model, although ascorbyl palmitate, firstly, is insoluble in the oil at these temperatures and, secondly, is as anionic emulsifier uncharged under these pH conditions and therefore exhibits only a very low emulsion-stabilization activity and also a low solubility in the aqueous medium. Lastly, it was similarly found that the polysorbate phase, for instance in the case of polysorbate 80, separates from the sterol ester phase, but that the addition of lecithin to the system prevents the separation and very distinctly improves the self-emulsifying properties in comparison to when the substances are each individually used alone.

In summary, it can be stated that the combination of ascorbyl fatty acid ester, preferably ascorbyl palmitate, and also lecithin and polysorbate, preferably polysorbate 80, gives rise to particularly good properties such as in particular very good self-emulsifying properties of a sterol ester formulation comprising oil as further component, and said combination is therefore a very particularly preferred embodiment (embodiment A) of the present invention, wherein the aforementioned proportions (the broad ranges and also the respectively disclosed narrower and preferred limits, such as in particular also combinations of the respectively preferred ranges of the various components) are to be observed and the, if necessary, further optional ingredients may be present. In an especially preferred embodiment AA, none of the optional further ingredients is present.

EXAMPLES

Production of the Formulations

Phytosterol ester and emulsifiers were combined and heated to 60° C. in order to avoid crystallization and/or, preferably and to reduce viscosity. Thereafter, mixing was carried out (Thinky mixer ARE-250 (Thinky Corporation, USA) at 2000 rpm for 1 min, or in an Ultra-Turrax tube drive (IKA, Germany) at 2000 rpm for about 30 min). The Thinky mixer was used when all input materials are present as liquid, whereas the Ultra-Turrax mixer was used when at least one of the input materials was present as semisolid or solid substance and could not easily dissolve in the liquid phytosterol ester phase or phytosterol ester phase liquefied at about 60° C. (e.g., protein, ascorbyl palmitate). The formulation was brought to room temperature (about 20 to 25'C) in order to allow any possible foam formation during production to dissolve overnight (i.e., after about 8 to 12 hours), and examined for phase separation. If no phase separation was apparent, the application tests described below were carried out.

All the results shown below have the numerical data in percent by weight.

Application Tests
Artificial Stomach Solution:
  2 g of a 1 M hydrochloric acid were added to 900 ml of distilled water, the pH was adjusted to 1.6 with 1 M hydrochloric add, and distilled water was used to top up to 1 liter.
Small Intestine Solution:
  0.42 g of NaOH flakes, 3.95 g of $NaH_2PO_4*H_2O$ and 6.19 g of NaCl were dissolved in 900 ml of distilled water. The pH was adjusted to 6.5 with sodium hydroxide solution and the solution was topped up to 1 liter using distilled water.
Testing in the Stomach Model:
  The phytosterol ester/emulsifier formulation was heated to about 60° C. in order to obtain a uniform liquid phase. Then, 100 ml of the stomach solution and 100 ml of the small intestine solution were each heated to 37-38° C., and 1 g of the formulation was added in each case. The systems were stirred at 200 rpm for one hour and then visually inspected.
  For the results, see Table 3.
Caco2 Model
  The formulations were likewise tested in the so-called Caco2 model. This involves examining the effect of the administration of a formulation on the uptake of cholesterol into Caco2 cells. This is a measure of whether and how well the sterol esters in the formulation can lower the cholesterol uptake of the cells. The higher the prevention of the (i.e., the lower the) cholesterol uptake, the more effective a formulation.
Principle Behind the Caco2 Testing:
  Cultivation of the Caco2 cells on a porous membrane; polarized structure of the cells, which take up nutrients (in this case: cholesterol) on the apical side and secrete them on the basal side.
  What is examined is the extent to which the transport of cholesterol is influenced by the simultaneous supplementation of phytosterols in combination with various vehicles.
  Testing steps: cultivation of the cells; production of the so-called mixed micelles; determination of the cytotoxicity and determination of the working concentration; measurement of the cholesterol concentration in the basal compartment (6 and 24 hours after the start of the supplementation) in 2 passes, triplicate measurement in each case.
  Cytotoxicity test: it was possible to use concentrations of 150 μg/ml of all the test substances without impairment of the cells; working concentrations 50-100-150 μg/ml were selected.
  For the formation of the micelles, the amount of cholesterol used for all treatment groups was kept constant. During the analysis of the apically applied solutions, it was established that the cholesterol content in the produced micelles varies (possibly caused by the intended mutual displacement of cholesterol and phytosterols during the micelle formation).

The results of the cholesterol uptake or of the transport through were therefore corrected to the actual cholesterol content of the supplementation solutions.

Sterol Ester Used:

Vegapure 95 E, from BASF SE, comprises small amounts of various tocopherols and ascorbyl palmitates as antioxidant; proportion of sterol ester: at least 97% (area percentage); proportion of free sterol: up to 6% (area percentage).

Solubilizers Used:

Polysorbate 20: polyoxyethylene (20) sorbitan monolaurate, E432

Polysorbate 80: polyoxyethylene (20) sorbitan monooleate, E433, "Tween 80"

Lipoid P 75: lecithin fraction and phospholipids from soybeans, comprises about 75% phosphatidylcholine, 7% phosphatidylethanolamine Prefera SSL 6000: sodium stearoyl-2-lactylate having a degree of esterification of 100 to 140

Lametop P 65: FDA-specification DATEM (DATEM=diacetyl tartaric acid ester of mono- and diglycerides), E472e Phosal 40 IP: liquid composition comprising about 40 percent soybean phophatidylcholine and sunflower oil and also mixed tocopherols MCT: medium chain triglycerides, an oil comprising predominantly C8 to C10 fatty acids Lecico SUN FM 580: sunflower lecithin from Lecico; liquid, enzymatically modified sunflower lecithin, 56% AU CholestOff: commercially available comparative product from NatureMade, USA; comprising plant sterols and stanols.

The following Table 1 (1a and 1b) shows tested formulations.

TABLE 1a

Compositions

| | | in gram | | | | |
|---|---|---|---|---|---|---|
| No. | Vehicle | Vegapure 95 E | Propylene glycol | MCT | Water | Sum total |
| 1 | Polysorbate 20 | 7.5 | 31.5 | 0 | 0 | 0 | 39 |
| 2 | Prefera SSL 6000 | 7.5 | 31.5 | 0 | 0 | 0 | 39 |
| 3 | Polysorbate 80 + water | 3.75 | 31.5 | 0 | 0 | 3.75 | 39 |
| 4 | Polysorbate 80 | 7.5 | 31.5 | 0 | 0 | 0 | 39 |
| 5 | Lametop P 65 + MCT | 3.75 | 31.5 | 0 | 3.75 | 0 | 39 |
| 6 | Lametop P 65 + propylene glycol | 3.75 | 31.5 | 3.75 | 0 | 0 | 39 |
| 7 | Lametop P 65 | 7.5 | 31.5 | 0 | 0 | 0 | 39 |
| 8 | Phosal 40 IP | 7.5 | 31.5 | 0 | 0 | 0 | 39 |
| 9 | Lipoid P 75 + water | 0.63 | 31.5 | 0 | 0 | 6.87 | 39 |

TABLE 1b

Compositions (continuation of Table 1a)

| | | Percent by weight | | | | | |
|---|---|---|---|---|---|---|---|
| No. | Vehicle | Vehicle | Vegapure 95 E | Propylene glycol | MCT | Water | Sum total |
| 1 | Polysorbate 20 | 19.23% | 80.77% | 0.00% | 0.00% | 0.00% | 100.00% |
| 2 | Prefera SSL 6000 | 19.23% | 80.77% | 0.00% | 0.00% | 0.00% | 100.00% |
| 3 | Polysorbate 80 + water | 9.62% | 80.77% | 0.00% | 0.00% | 9.62% | 100.00% |
| 4 | Polysorbate 80 | 19.23% | 80.77% | 0.00% | 0.00% | 0.00% | 100.00% |
| 5 | Lametop P 65 + MCT | 9.62% | 80.77% | 0.00% | 9.62% | 0.00% | 100.00% |
| 6 | Lametop P 65 + propylene glycol | 9.62% | 80.77% | 9.62% | 0.00% | 0.00% | 100.00% |
| 7 | Lametop P 65 | 19.23% | 80.77% | 0.00% | 0.00% | 0.00% | 100.00% |
| 8 | Phosal 40 IP | 19.23% | 80.77% | 0.00% | 0.00% | 0.00% | 100.00% |
| 9 | Lipoid P 75 + water | 1.62% | 80.77% | 0.00% | 0.00% | 17.62% | 100.00% |

Results of the Tests:

Table 1 (1a and b): tested formulations—composition

FIG. 1: Cholesterol content of the basal recipient medium after 6 hours (in % of the applied starting concentration)

Figure 2:
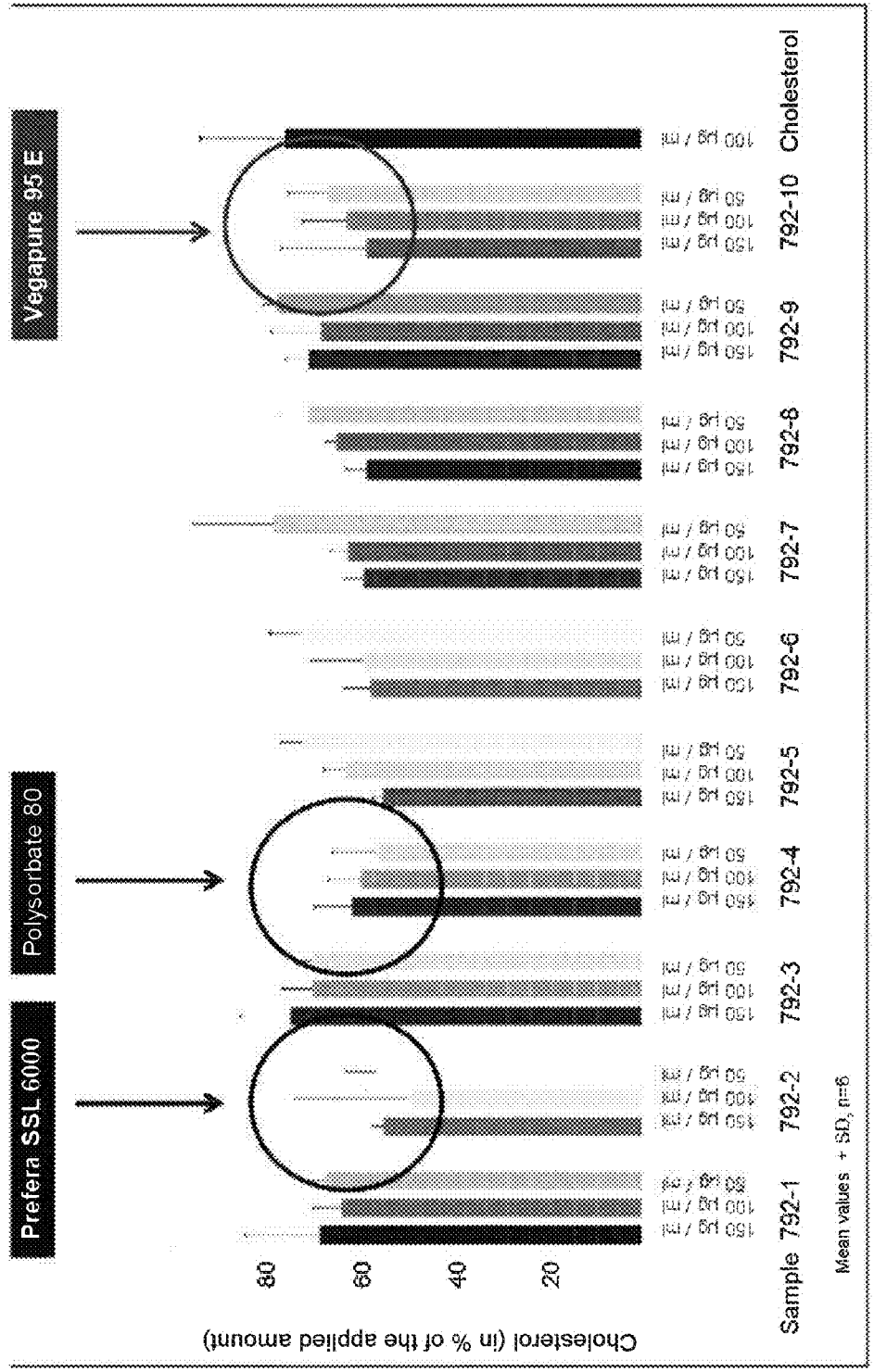

FIG. 2: Cholesterol content of the basal recipient medium after 24 hours (in % of the applied starting concentration)

Figure 3:
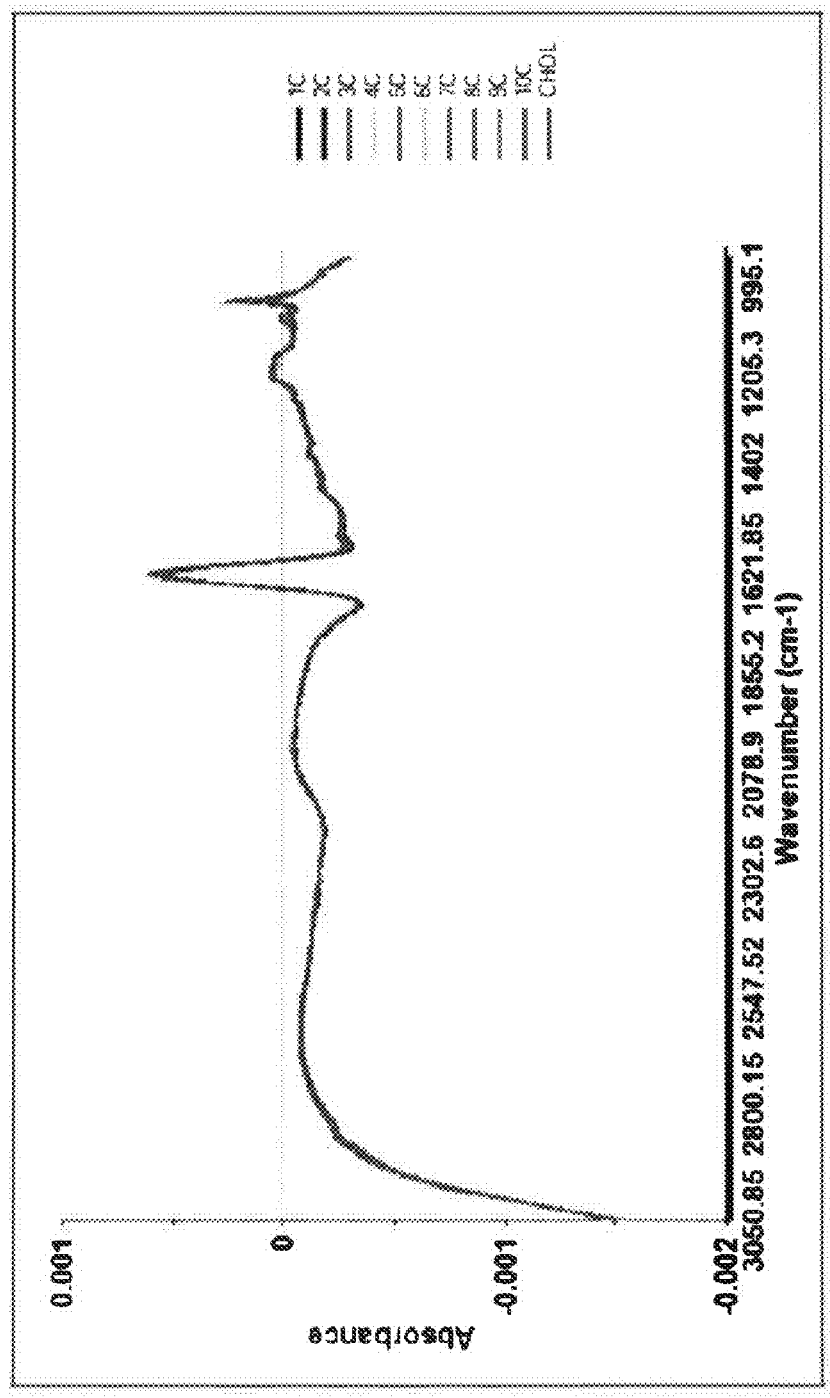

FIG. 3: Infrared spectra of the micelle solutions of cholesterol ("CHOL") alone and in combination with the tested formulations FIG. 4: PCA analysis of the micelle solutions of cholesterol (CHOL) alone and in combination with various test substances (C1 to C10)

FIG. 5: Results relating to Table 4

Further results from the Caco2 model (figure relating to Table 3)

Table 2: Influencing of the transport of cholesterol by the phytosterol-vehicle combination in comparison with Vegapure 95E as individual substance Table 3: Further results from the Caco2 model Table 4: Results of the testing in the stomach model ("Sterol ester"=Vegapure 95 E from BASF)

TABLE 2

Influencing of the transport of cholesterol by the phytosterol-vehicle combination in comparison with Vegapure 95E as individual substance

| Formulation comprising as solubilizers | Dosage of the test substance | After 6 hours | | After 24 hours | |
|---|---|---|---|---|---|
| | | Cholesterol in the recipient compartment (% of the amount used) | % less cholesterol than Vegapure 95E without vehicle | Cholesterol in the recipient compartment (% of the amount used) | % less cholesterol than Vegapure 95E without vehicle |
| Cholesterol control | | 78.72 | | 76.11 | |
| No solubilizer (only Vegapure 95 E) | 50 µg/ml | 70.85 | | 67.62 | |
| | 100 µg/ml | 70.79 | | 63.54 | |
| | 150 µg/ml | 66.32 | | 59.05 | |
| Prefera SSL 6000 | 50 µg/ml | 54.46 | 23% | 56.96 | 16% |
| | 100 µg/ml | 54.46 | 23% | 59.97 | 6% |
| | 150 µg/ml | 45.10 | 32% | 55.46 | 6% |
| Polysorbate 80 | 50 µg/ml | 59.23 | 16% | 56.77 | 16% |
| | 100 µg/ml | 66.56 | 6% | 60.32 | 5% |
| | 150 µg/ml | 65.02 | 2% | 62.11 | n.a. |
| Lametop P65 + MCT | 50 µg/ml | 69.41 | 2% | 72.51 | n.a. |
| | 100 µg/ml | 53.04 | 25% | 63.92 | n.a. |
| | 150 µg/ml | 50.74 | 23% | 55.64 | 6% |
| Phosal 40 IP | 50 µg/ml | 57.76 | 18% | 71.85 | n.a. |
| | 100 µg/ml | 53.88 | 24% | 65.75 | n.a. |
| | 150 µg/ml | 49.67 | 25% | 58.78 | 0% |

Measurement of the Displacement of Cholesterol by Phytosterol During the Micelle Formation Cholesterol and phytosterols are poorly water-soluble and are transported in the body together with fatty acids and bile salts in the mixed micelles.

The displacement of cholesterol from the micelles is seen as an important mechanism of action of the phytosterols for the lowering of cholesterol.

The goal of the measurement is to determine the influence of the test substances on the cholesterol concentration in the micelle solution obtained in order to thus obtain an indication of the possible displacement of the cholesterol from the micelles.

The test substances were used in 5 different concentrations together with a defined cholesterol concentration for in vitro micelle formation.

The micelle emulsions obtained were examined by infrared spectroscopy using the SpeCCs analyzer (Cetics Healthcare).

At first glance, the infrared spectra (FIG. 3) differ only slightly owing to the similarity in the chemical structure of cholesterol and phytosterols. Further evaluation is done statistically using principal-component analysis (PC), by means of which it is possible to determine the similarity of samples.

Figure 4:
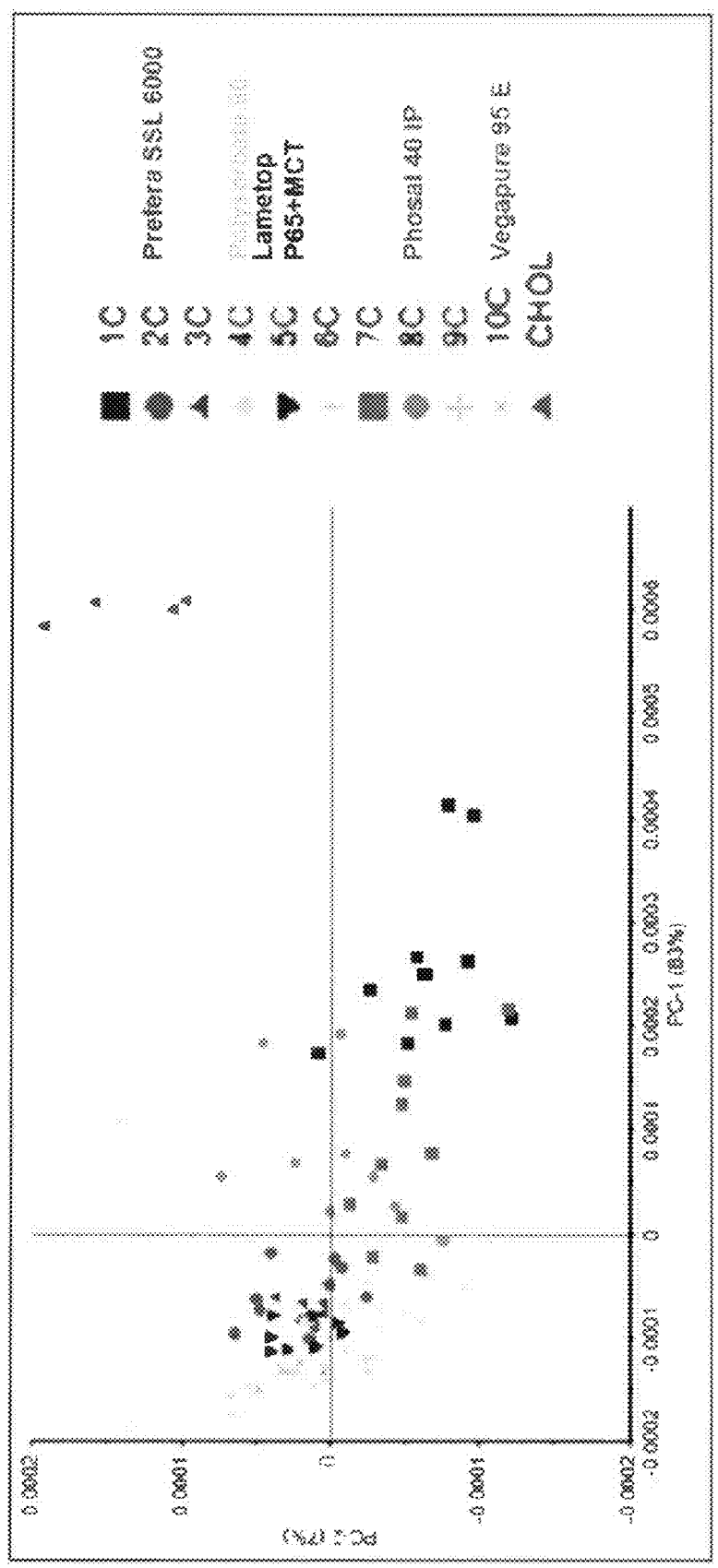

PCA analysis of the micelle solutions of cholesterol (CHOL) alone and in combination with various test substances (C1 to C10) (FIG. 4)

Result: The formulation comprising Lipoid P75+water differs most distinctly from the pure cholesterol micelles, followed by Vegapure 95 E, polysorbate 80, Lametop P65+ MCT and Prefera SSL 6000, and this can be seen as a measure of the displacement of cholesterol from the micelles.

TABLE 3

Caco2 model preliminary results - influencing of the transport of cholesterol by combinations of phytosterol esters and emulsifiers

| Formulations tested | Dosage of the test substance (µg/ml) | Cholesterol concentration in the recipient medium in µg/ml (after 6 hours) | Cholesterol concentration in the recipient medium in µg/ml (after 24 hours) |
|---|---|---|---|
| Experiment 88; Vegapure 95 E (without emulsifier) | 150 | 69.9 | 64.9 |
| Experiment 88; Vegapure 95 E (without emulsifier) | 100 | 65.0 | 64.7 |
| Experiment 88; Vegapure 95 E (without emulsifier) | 50 | 68.2 | 64.4 |
| Experiment 89: Vegapure 95 E with Lipoid 75 and sunflower oil | 150 | 63.2 | 63.3 |
| Experiment 89: Vegapure 95 E with Lipoid 75 and sunflower oil | 100 | 65.7 | 61.0 |
| Experiment 89: Vegapure 95 E with Lipoid 75 and sunflower oil | 50 | 62.7 | 59.4 |
| Experiment 100: Vegapure 95 E and Lecico SUN FM 580 and Tween 80 | 150 | 61.3 | 57.4 |
| Experiment 100: Vegapure 95 E and Lecico SUN FM 580 and Tween 80 | 100 | 60.6 | 60.1 |

TABLE 3-continued

Caco2 model preliminary results - influencing of the transport of cholesterol by combinations of phytosterol esters and emulsifiers

| Formulations tested | Dosage of the test substance (μg/ml) | Cholesterol concentration in the recipient medium in μg/ml (after 6 hours) | Cholesterol concentration in the recipient medium in μg/ml (after 24 hours) |
|---|---|---|---|
| Experiment 100: Vegapure 95 E and Lecico SUN FM 580 and Tween 80 | 50 | 57.2 | 58.6 |
| CholestOff (commercially available comparative product) | 150 | 59.42 | 60.4 |
| CholestOff (commercially available comparative product) | 100 | 56.93 | 58.3 |
| CholestOff (commercially available comparative product) | 50 | 60.66 | 60.5 |

The results in Table 3 show that the transport of cholesterol can be influenced more greatly when using a combination of phytosterol ester and emulsifier(s) than by the phytosterol ester alone.

Table 4 shows the assessment of the testing of the formulations from Table 3.

FIG. 5 shows selected results in the Caco2 test of formulations from Table 3.

Evaluation relating to Table 4: Visual assessment scale

1=Homogeneous, no oil on the surface
2=Largely homogeneous with small to moderate oil droplets on the surface
3=Moderate turbidity, noticeable oil layer on the surface
4=Slightly whitish-turbid appearance, thick oil layer on the surface
5=No emulsification effect, i.e., virtually complete phase separation

TABLE 4

Results of the testing in the stomach model ("Sterol ester" = Vegapure 95 E from BASF); see also FIG. 5

| Experiment number | Sterol ester concentration (% by weight) | Input material 1 | Input material 1 conc. (% by weight) | Input material 2 | Input material 2 conc. (% by weight) | Input material 3 | Input material 3 conc. (% by weight) |
|---|---|---|---|---|---|---|---|
| 88 | 100 | Vegapure 95E | 100 | | | | |
| 89 | 80 | P75 | 1.6 | Sunflower oil | 17.6 | | |
| 90 | 80 | Lecico SUN FM 580 | 20 | | | | |
| 91 | 85 | Lecico SUN FM 580 | 15 | | | | |
| 92 | 90 | Lecico SUN FM 580 | 10 | | | | |
| 93 | 80 | Tween 80 | 20 | | | | |
| 94 | 98 | Tween 80 | 2 | | | | |
| 95 | 90 | Ascorbyl palmitate | 10 | | | | |
| 96 | 98 | Ascorbyl palmitate | 2 | | | | |
| 97 | 80 | Lecico SUN 400 | 20 | | | | |
| 98 | 80 | Lecico SUN FM 580 | 19 | Tween 80 | 1 | | |
| 99 | 80 | Lecico SUN FM 580 | 18 | Tween 80 | 2 | | |
| 100 | 80 | Lecico SUN FM 580 | 16 | Tween 80 | 4 | | |
| 101 | 80 | Lecico SUN FM 580 | 18 | Ascorbyl palmitate | 2 | | |
| 102 | 80 | Lecico SUN FM 580 | 16 | Ascorbyl palmitate | 4 | | |
| 103 | 80 | Lecico SUN FM 580 | 12 | Ascorbyl palmitate | 8 | | |
| 104 | 80 | Lecico SUN FM 580 | 8 | Ascorbyl palmitate | 12 | | |
| 105 | 85 | Lecico SUN FM 580 | 13.5 | Ascorbyl palmitate | 1.5 | | |
| 106 | 90 | Lecico SUN FM 580 | 9 | Ascorbyl palmitate | 1 | | |
| 107 | 80 | Lecico SUN FM 580 | 16 | Ascorbyl palmitate | 2 | Tween 80 | 2 |
| 108 | 80 | Lecico SUN FM 580 | 19 | Systerna SP70 | 1 | | |

TABLE 4-continued

Results of the testing in the stomach model ("Sterol ester" = Vegapure 95 E from BASF); see also FIG. 5

| 109 | 80 | Lecico SUN FM 580 | 18 | Systerna SP70 | 2 |

| Experiment number | Stomach solution: turbidity (NTU) | Stomach solution: visual assessment | Intestine solution: turbidity (NTU) | Intestine solution: visual assessment |
| --- | --- | --- | --- | --- |
| 88 | 0.3 | 5 | 1 | 5 |
| 89 | 485 | 2 | 317 | 3 |
| 90 | 266 | 3 | 1000 | 2 |
| 91 | 59 | 4 | 763 | 3 |
| 92 | 71 | 4 | 492 | 4 |
| 93 | 63 | 4 | 111 | 4 |
| 94 | 102 | 3 | 27 | 4 |
| 95 | 9.2 | 4 | 1000 | 2 |
| 96 | 1.1 | 5 | 90 | 4 |
| 97 | 31 | 4 | 814 | 2 |
| 98 | 554 | 2 | 1000 | 1 |
| 99 | 1000 | 1 | 1000 | 1 |
| 100 | 769 | 2 | 1000 | 1 |
| 101 | 25 | 4 | 922 | 2 |
| 102 | 237 | 2 | 46 | 5 |
| 103 | 516 | 2 | 50 | 5 |
| 104 | 1000 | 3 | 1000 | 1 |
| 105 | 43 | 4 | 679 | 2 |
| 106 | 18 | 5 | 379 | 3 |
| 107 | 383 | 2 | 1000 | 2 |
| 108 | 375 | 2 | 830 | 2 |
| 109 | 51 | 4 | 539 | 3 |

The invention claimed is:

1. A formulation for gel capsules comprising at least 61% by weight sterol ester and at least two solubilizers selected from the group consisting of polysorbates, lecithins, sodium stearoyl-2-lactylates, fatty acid esters of ascorbic acid, fatty acid esters of isoascorbic acid, and sugar esters with fatty acids.

2. The formulation according to claim 1, wherein the sterol ester has been obtained from sterols of plant origin (phytosterols) or the hydrogenated analogs thereof, the stanols.

3. The formulation according to claim 2, wherein the sterol ester has been obtained from sterols.

4. The formulation according to claim 1, wherein the sterol ester is obtained by esterification of fatty acids of natural origin.

5. The formulation according to claim 4, wherein the fatty acids are monounsaturated or polyunsaturated fatty acids.

6. The formulation according to claim 5, wherein the fatty acids comprise omega-3 fatty acids in an amount of at least 30 percent by weight, based on the fatty acid portion.

7. The formulation according to claim 1, wherein, at least one of the at least two solubilizers is selected from the group consisting of polysorbates, lecithins, sodium stearoyl-2-lactylates, and combinations thereof.

8. The formulation according to claim 7, comprising at least one wherein at least one of the at least two solubilizers is selected from the group consisting of fatty acid esters of ascorbic acid, fatty acid esters of isoascorbic acid, and sugar esters with fatty acids.

9. The formulation according to claim 1, wherein the at least two solubilizers are selected from the group consisting of ascorbyl fatty acid ester, lecithin, and polysorbate.

10. The formulation according to claim 1, wherein the formulation comprises water or oil, and wherein, the water or oil is present in an amount of not more than 15% by weight, based on the formulation.

11. A gel capsule comprising the formulation according to claim 1.

12. The gel capsule according to claim 11 in the form of a soft or hard capsule.

13. The gel capsule according to claim 11 for use as food supplement or as pharmaceutical.

14. A process for producing a formulation according to claim 1, comprising:
   (a) combining sterol ester and the at least two solubilizers to form a mixture,
   (b) heating the mixture to a temperature above the melting point of the sterol ester, and
   (c) mixing the heated mixture at 500 to 2500 rpm for 1 to 60 minutes to obtain a uniform mixture.

15. A process for producing a gel capsule according to claim 11, comprising:
   (a) combining sterol ester and the at least two solubilizers to form a mixture,
   (b) heating the mixture to a temperature above the melting point of the sterol ester, and
   (c) mixing the heated mixture at 500 to 2500 rpm for 1 to 60 minutes to obtain a uniform mixture; and
   (d) incorporating the uniform mixture into a gel capsule.

16. The formulation according to claim 1, wherein the sterol ester is obtained by esterification of fatty acids of plant or marine origin.

17. The formulation according to claim 8, comprising ascorbyl palmitate, lecithin and polysorbate 80.

18. The formulation according to claim 1, wherein the at least two solubilizers are lecithin and polysorbate.

19. The formulation according to claim 18, wherein the polysorbate is polysorbate 80.

* * * * *